United States Patent
Alexandre et al.

(10) Patent No.: US 6,537,245 B1
(45) Date of Patent: Mar. 25, 2003

(54) NEEDLELESS SYRINGE WITH A FRICTION ACTIVATED PYROTECHNIC INITIATOR

(75) Inventors: Patrick Alexandre, Gray (FR); Bernard Brououieres, Toulon (FR); Philippe Gautier, Le Plessis Pate (FR)

(73) Assignee: Crossject Company, Paris (FR)

( * ) Notice: Subject to any disclaimer, the term of this patent is extended or adjusted under 35 U.S.C. 154(b) by 154 days.

(21) Appl. No.: 09/680,302

(22) Filed: Oct. 6, 2000

(30) Foreign Application Priority Data

Oct. 8, 1999 (FR) ............................................. 99 12559

(51) Int. Cl.⁷ ................................................ A61M 5/30
(52) U.S. Cl. ............................ 604/69; 604/68; 604/145
(58) Field of Search ............................ 604/68, 69, 140, 604/141, 143, 145

(56) References Cited

U.S. PATENT DOCUMENTS

| 2,322,244 A | 6/1943 | Lockhart |
|---|---|---|
| 3,145,712 A | 8/1964 | Litz |
| 3,308,818 A | 3/1967 | Rutkowski |
| 3,335,722 A | 8/1967 | Lowery et al. |
| 3,802,430 A | * 4/1974 | Schwebel et al. ....... 128/173 H |
| 4,089,334 A | 5/1978 | Schwebel et al. |
| 4,124,024 A | * 11/1978 | Schwebel et al. ....... 128/173 H |

FOREIGN PATENT DOCUMENTS

| CH | 681 175 | 7/1990 |
|---|---|---|
| FR | 2 393 261 | 12/1978 |
| FR | 2 487 968 | 2/1982 |

* cited by examiner

Primary Examiner—Gregory Huson
Assistant Examiner—Huyen Le
(74) Attorney, Agent, or Firm—Pillsbury Winthrop LLP

(57) ABSTRACT

A needleless syringe equipped with an initiating device comprising a triggering device and a pyrotechnic charge, wherein the triggering device contains a triggering member connected to a friction igniter that initiates the pyrotechnic charge by friction. An advantage of the invention is that the syringe produces very limited amounts of noise during operation.

10 Claims, 1 Drawing Sheet

NEEDLELESS SYRINGE WITH A FRICTION ACTIVATED PYROTECHNIC INITIATOR

The technical field of the invention is that of needleless syringes intended to inject solid, liquid or mixed particles of active principle through the skin for therapeutic use.

Specifically, the invention relates to a needleless syringe operating on the basis of an initiating device involving a triggering device associated with a pyrotechnic charge. More especially, this triggering device is to be suited to the firing of a pyrotechnic charge housed in a lightweight small sized object and which has to be actuated manually.

The solution proposed by the invention recommends the use of a friction igniter as a main part of the triggering device for triggering the needleless syringe.

It would seem that, in the field of needleless syringes, there is no patent relating to the use of a friction igniter in the triggering device of such syringes. However, other types of triggering device have already been developed for needleless syringes involving a pyrotechnic charge. Mention may, for example, be made of U.S. Pat. No. 2,322,244 relating to a needleless hypodermic injector operating on the basis of a blank cartridge, the firing of which is brought about by the percussion of a piston brought up to speed by the relaxation of a spring, this firing being triggered manually by first of all contracting the said spring using a button. The liquid to be injected which is in contact with the cartridge is expelled from the injector under the effect of the pressure generated by the combustion gases. U.S. Pat. No. 4,089,334, for its part, describes a needleless injector equipped with a pyrotechnic charge, the firing of which is brought about by a primary charge, itself initiated by percussion of a rigid rod set in motion by the relaxation of a spring. The gases emitted by the pyrotechnic charge expand in a downstream chamber, setting in motion a piston whose movement causes the liquid product that is to be injected to be expelled. These two patents tend to show that percussion triggering devices involving, in particular, a spring, a solid component acting as striker and at least one pyrotechnic charge, are well known in the field of needleless syringes.

Finally, it is beneficial to mention U.S. Pat. No. 3,145,712 which relates to a device for the transcutaneous injection of medicinal product intended at supplementing suits that provide protection against gas attack. These devices are carried by the individual and can be triggered either manually or automatically if gas is detected. These devices operate on the basis of a pyrotechnic cartridge fired by a primary charge, this being initiated electrically by a current created between two carefully located terminals within this primary charge. The gases generated by the combustion of the pyrotechnic charge create a pressure which serves to eject the liquid medicinal product.

By contrast, the use of a friction igniter for initiating a pyrotechnic charge in objects such as, for example, flares, grenades or mines, is known and has been the subject of numerous patents. Mention may, among others, be made of French Patent FR 2 393 261 which relates to an undetectable mine for tracked vehicles which can be triggered by a friction wiper whose movement in contact with a detonator will contribute to its initiation.

Likewise, French Patent FR 2 487 968 describes an igniter cap particularly suited to the firing of grenades and containing, in particular, an ignition pyrotechnic chain the first element of which is a pyrotechnic charge which can be initiated by friction.

Needleless syringes need to be endowed with a triggering device which can be actuated manually and which makes it possible to dispense with an excessively energetic or bulky activation source while at the same time remaining reliable and performing well. In effect, the customary triggering devices used involve detonators whose primary composition is particularly sensitive. In storage situations, these syringes may therefore carry a risk of inadvertent operation, because of the high sensitivity of the detonator to external influences such as high temperatures or droppage. Furthermore, in spite of their sensitivity, the detonators, to be initiated, require a relatively bulky percussion device. In order to solve this bulk problem and this risk of inadvertent operation, it has been discovered that it is possible to miniaturize a friction initiator, achieved with good safety, and which triggers with excellent reliability. This friction initiation occurs gently, by directly igniting the pyrotechnic charge, without having to resort to a shock wave as was the case in initiation with a detonator. This has, as a direct and advantageous consequence, the effect that the noise produced when using the syringe is extremely limited. Finally, the needleless syringe according to the invention, having a friction triggering device, has a double safety feature; one of the features is in the form of a retractable component preventing any depression of the trigger and the other is in the form of an area of roughness requiring particular effort to depress the trigger once the retractable component has been removed.

The needleless syringe according to the invention has all these technical characteristics which are particularly well suited to needleless injection.

The subject of the present invention is a needleless syringe equipped with an initiating device comprising a triggering device and a pyrotechnic charge, characterized in that the triggering device comprises a triggering member connected to a friction means of the pyrotechnic charge. The friction means consists of a component whose main function is to rub against a pyrotechnic charge with the purpose of directly initiating it. A device such as this requires a friction-sensitive pyrotechnic composition such as zirconium-based compositions, for example. Advantageously, the friction means is a friction igniter. As a preference, the friction igniter consists of an elongate component one end of which has asperities. As a preference, the component is rigid and has an approximately cylindrical shape. Advantageously, the component is secured to the triggering member so that its movement is dictated by the movement imparted to the said member.

According to one preferred embodiment of the invention, the triggering member is a push-button intended to be actuated manually and capable of sliding along an elongate hollow central body in which the pyrotechnic charge is housed. In the "storage" configuration for which the needleless syringe has not yet operated, the friction igniter is distant from the pyrotechnic charge. This charge will be ignited when the friction igniter comes into contact with it, giving rise to direct mechanical friction.

As a preference, the push-button is placed at one of the ends of the central body to make it easier to actuate, and more especially is placed at the opposite end to the end via which the active principle is injected. Advantageously, the friction igniter and the pyrotechnic charge are aligned along the axis of the hollow body. As a preference, the friction igniter and the pyrotechnic charge have a roughly cylindrical shape and their axis is coincident with the axis of the hollow body. Advantageously, an area of roughness located between the push-button and the central body makes it possible to increase the friction forces between the two elements as one slides along the other. In more concrete terms, this area allows the introduction of resistance preventing any initiation so long as sufficient effort is not applied for sufficiently long to depress the friction igniter and bring it into contact with the pyrotechnic charge.

As a preference, the area of roughness consists of the fitting-together of annular asperities of one of the two elements into grooves in the other element which are designed to accommodate them, so as to entail a minimum level of pressure required to begin to depress the push-button. This avoids inadvertent triggering as a result of mild or unintentional stressing when the needleless syringe is rendered operational by removing the retractable stop which protects the end via which the active principle is injected.

Specifically, and as a preference, the push-button has a safety feature in the form of a retractable stop preventing any movement of the said button. The other function of this safety feature is to protect the end of the syringe from which the active principle is to be ejected.

Advantageously, the retractable stop consists of a cap equipped with a collar immobilizing the push-button. A circular line of weakness allows the collar to be detached from the cap. The collar is rigid and has a tag for tearing it. Advantageously, the annular asperities constituting the area of roughness have the particular feature of preferably deforming along the axis of thrust and of therefore having a non-return effect. Thus, the user does not run the risk of being subjected to the effects of the abrupt retreat of the push-button. As a preference, the friction igniter is made of stainless steel.

Needleless syringes according to the invention have the advantage of producing a pyrotechnic reaction which is not as violent as the reaction perceived during operation of a percussion detonator. This is because they allow the gas-generating composition to be initiated gently by friction rather than via a shock wave.

In addition, as they are triggered and as they operate, they give rise to an extremely limited amount of noise.

Finally, they have the advantage of being placed on the civilian market without being subject to the constraints inherent to devices involving explosives or detonating compositions.

A detailed description of a preferred embodiment of the invention is given hereinbelow with reference to FIGS. 1 and 2.

Figure 1:
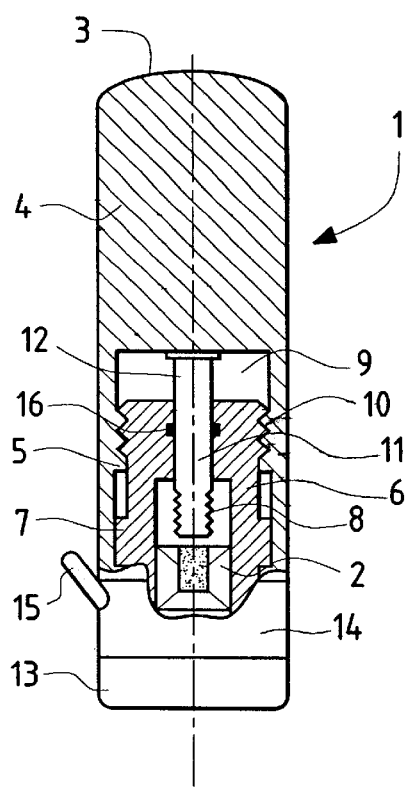
FIG. 1 is a view in longitudinal axial cross section of a needleless syringe according to the invention, and which has not yet operated.
Figure 2:
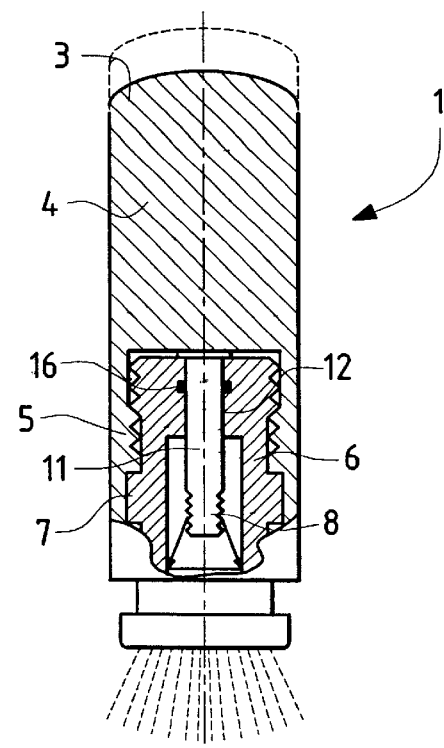
FIG. 2 is a view in longitudinal axial cross section of the syringe of FIG. 1, once it has operated.

Referring to FIG. 1, according to the preferred embodiment of the invention, the needleless syringe 1 has an upstream part comprising a triggering device and a downstream part comprising a pyrotechnic charge 2, the active principle in solid or liquid form, an ejection nozzle and a guide for applying to the skin. The triggering device includes a push-button 3 and a friction means in the form of a friction igniter 12.

The push-button 3 has a roughly cylindrical shape and consists of a solid part 4 extended by a hollow cylindrical part 5 of identical outside diameter. This hollow cylindrical part 5 of constant outside diameter comprises an internal shoulder to demarcate a very thick hollow rear cylinder in continuity with a much thinner hollow front cylinder, the rear cylinder lying between the solid part 4 and the front cylinder. The rear cylinder has, on its internal side wall, a region exhibiting a series of annular asperities. The hollow cylindrical part 5 over part of its length surrounds a hollow cylindrical body 6 which, on its external side wall, has a region also exhibiting a series of annular asperities, the said body 6 being continued by a broadened cylindrical base 7.

The hollow cylindrical body 6 comprises an internal shoulder demarcating an upstream duct of small diameter in continuity with a downstream duct of larger diameter in which the pyrotechnic charge 2 is housed. This pyrotechnic charge 2 is split into two distinctive parts, one of them, relating to a friction-sensitive zirconium-based composition and the other relating to a gas-generating composition which will be used to expel the particles. The friction igniter 12 consists of an elongate component 11 of cylindrical shape having a free end 8, equipped with asperities, and is implanted in the solid part 4 of the push-button 3 so that it lies in the hollow cylindrical part 5 of the said button 3, in a central position in which their two axes are coincident.

The push-button 3 surrounds the hollow cylindrical body 6 in such a way that their respective regions displaying annular asperities correspond with one another and nest together and so that a gap 9 remains between the solid part 4 of the push-button 3 and the end of the hollow cylindrical body 6 facing it.

The fitting-together of these two areas makes it possible to create an area of roughness 10 consisting of hard points, so as to increase the friction forces as the push-button 3 slides along the hollow cylindrical body 6. These annular asperities constituting the area of roughness 10 have the particular feature of preferably deforming along the axis of thrust and therefore of having a non-return effect. The external side wall of the broadened base 7 of the hollow cylindrical body 6 is in contact with the internal side wall of the front cylinder of the hollow cylindrical part 5 of the push-button 3 and the end of the front cylinder is in contact with the base 7 so as to prevent the push-button 3 from easily being pulled out of the syringe 1.

The friction igniter which is fixed to the solid part 4 of the push-button 3 passes through the upstream duct of the hollow cylindrical body 6 and its free end 8 equipped with asperities emerges into the downstream duct of the said body 6 a certain distance away from the pyrotechnic charge 2. A seal 16, placed in a circular groove in the upstream duct, presses against the friction igniter 12 so as to make a good seal between the downstream duct in which combustion will take place and the gap 9 between the push-button 3 and the end of the hollow cylindrical body 6.

The syringe 1 has a safety feature in the form of a retractable stop consisting of a cap 13 equipped with a detachable rigid collar 14 which has the same diameter as the outside diameter of the push-button 3. The button 13, of cylindrical shape, fits around the sensitive end of the syringe 1 via which the active principle is expelled. The active principle, or at least its location in the syringe, is not depicted in the figures but whatever configuration is adopted, it is located downstream of the pyrotechnic charge 2, either in the path of the gases or to the side.

The collar 14 which is of cylindrical shape is secured to the cap 13, and is locked in place between the said cap 13 and the free end of the hollow cylindrical part 5 of the push-button 3.

An area of precutting, in the form of circular scoring, is made between the collar 14 and the cap 13 and a tab 15 fixed to the said collar 14 can easily be grasped by the user to assist in detaching the collar 14.

The way in which this preferred alternative form of syringe according to the invention works involves the following steps.

The user grasps hold of the tab 15 and pulls so as to separate the collar 14 from the cap 13 along the circular line of precutting. Once the collar 14 has been removed, the protective cap 13 is removed in turn and the syringe 1 is thus unlocked.

The downstream part of the syringe 1 is brought into contact with the skin of the patient who is to be treated. The user then exerts manual pressure on the push-button 3 at its solid part 4, so as to depress it. To do this, he has to provide effort to overcome the friction forces incurred by the area of roughness 10. When the push-button 3 begins to slide along the hollow cylindrical body 6, it gives rise to a linear movement of the friction igniter 12 in the hollow cylindrical body 6 until its free end 8 equipped with asperities reaches the pyrotechnic charge 2 at its part consisting of the friction-sensitive zirconium-based composition. This end 8, which acts as a friction wiper, causes friction within the said charge 2 which reacts by igniting. Thus, the gases generated by this combustion will initiate the gas-generating composition. The gases resulting from this second combustion will allow the active principle to be ejected through the patient's skin either, for example, by moving a piston to eject active principle in liquid form through a nozzle, or, for example, by creating a shock wave to accelerate particles of active principle in solid form. The maximum movement of the push-button 3 corresponds to the internal shoulder of the hollow cylindrical part 5 coming into abutment against the broadened base 7 of the hollow cylindrical body 6. As the annular asperities of the area of roughness 10 are designed to deform along the axis of thrust, they have a non-return effect so as, in particular, to allow the push-button 3 to remain depressed, maintaining its position with respect to the hollow cylindrical body 6. The circular seal 16 also makes it possible to prevent gases from coming back inadvertently towards the push-button 3.

What is claimed is:

1. Needleless syringe equipped with an initiating device comprising a triggering device and a pyrotechnic charge (2), characterized in that the triggering device comprises a triggering member (3) connected to a friction means (12) of the pyrotechnic charge (2) wherein the friction means (12) is a friction igniter with an elongated component (11) one end (8) of which has asperities.

2. Needleless syringe according to claim 1, characterized in that the component (11) is rigid and has an approximately cylindrical shape.

3. Needleless syringe according to claim 1, characterized in that the component (11) is secured to the triggering member (3) so that its movement is dictated by the movement imparted to the said member (3).

4. Needleless syringe according to claim 3, characterized in that the triggering member (3) is a push-button intended to be actuated manually and capable of sliding along an elongate hollow central body (6) in which the pyrotechnic charge (2) is housed.

5. Needleless syringe according to claim 4, characterized in that the push-button (3) is placed at one of the ends of the central body (6).

6. Needleless syringe according to claim 4, characterized in that the friction igniter (12) and the pyrotechnic charge (2) are aligned along the axis of the hollow body (6).

7. Needleless syringe according to claim 4, characterized in that an area of roughness (10) located between the push-button (3) and the central body (6) makes it possible to increase the friction forces between the two elements as one slides along the other.

8. Needleless syringe according to claim 4, characterized in that the push-button (3) has a safety feature in the form of a removable stop (13, 14) preventing any movement of said button (3).

9. Needleless syringe according to claim 8, characterized in that the removable stop consists of a cap (13) equipped with a detachable collar (14).

10. Needleless syringe according to claim 1, characterized in that the friction igniter (12) is made of stainless steel.

* * * * *

UNITED STATES PATENT AND TRADEMARK OFFICE
CERTIFICATE OF CORRECTION

PATENT NO.    : 6,537,245 B1
DATED         : March 25, 2003
INVENTOR(S)   : Alexandre et al.

It is certified that error appears in the above-identified patent and that said Letters Patent is hereby corrected as shown below:

<u>Title page,</u>
Item [75], Inventors, please correct the spelling of the name of the second inventor:
"Bernard Brououieres" should read as -- Bernard Brouquières --.

Signed and Sealed this

Fifteenth Day of July, 2003

JAMES E. ROGAN
*Director of the United States Patent and Trademark Office*